(12) United States Patent
Schuller (10) Patent No.: US 8,763,244 B2
(45) Date of Patent: Jul. 1, 2014

(54) METHOD OF FORMING CONDUCTIVE ELEMENTS

(75) Inventor: Peter Schuller, Turramurra (AU)

(73) Assignee: Cochlear Limited, Macquarie University, NSW (AU)

(*) Notice: Subject to any disclaimer, the term of this patent is extended or adjusted under 35 U.S.C. 154(b) by 785 days.

(21) Appl. No.: 12/472,053

(22) Filed: May 26, 2009

(65) Prior Publication Data

US 2009/0229739 A1 Sep. 17, 2009

Related U.S. Application Data

(63) Continuation of application No. 10/563,866, filed as application No. PCT/AU2004/000920 on Jul. 9, 2004, now abandoned.

(30) Foreign Application Priority Data

Jul. 9, 2003 (AU) ................................ 2003903532

(51) Int. Cl.
*H05K 3/02* (2006.01)
(52) U.S. Cl.
USPC .................. 29/847; 29/830; 29/874; 600/372
(58) Field of Classification Search
USPC ........... 29/830, 831, 846, 847, 874, 884, 885; 156/60, 155, 247; 174/254; 204/290.14; 250/426; 427/540; 600/25, 600/372
See application file for complete search history.

(56) References Cited

U.S. PATENT DOCUMENTS

| | | | |
|---|---|---|---|
| 3,443,055 A * | 5/1969 | Gwynn et al. | 204/290.14 |
| 3,749,101 A | 7/1973 | Williamson | |
| 3,902,078 A | 8/1975 | Peterson | |
| 4,502,492 A | 3/1985 | Bornzin | |
| 4,532,930 A | 8/1985 | Crosby et al. | |
| 5,118,400 A | 6/1992 | Wollam | |
| 5,433,836 A | 7/1995 | Martin et al. | |
| 5,628,778 A | 5/1997 | Kruse et al. | |
| 5,659,237 A | 8/1997 | Divan et al. | |
| 6,043,628 A | 3/2000 | Perelle et al. | |

(Continued)

FOREIGN PATENT DOCUMENTS

| | | |
|---|---|---|
| DE | 2720109 | 12/1977 |
| EP | 0175654 | 3/1986 |

(Continued)

OTHER PUBLICATIONS

Written Opinion; International Application No. PCT/AU2004/000920 mailed on Nov. 17, 2004 (4 pages).

(Continued)

*Primary Examiner* — Donghai D Nguyen
(74) *Attorney, Agent, or Firm* — K&L Gates, LLP (57) ABSTRACT

There is disclosed a method of forming a patterned conductive element for an implantable medical device, the method comprising the steps of: depositing a supplementary material on a sheet of conductive, parent material to form a sheet of composite material; applying a carrier material over the supplementary material of the composite sheet to form a sheet of semi-finished material; removing portions from at least the conductive parent material of the sheet of semi-finished material in accordance with a desired pattern corresponding to a patterned conductive element to be formed; and releasing at least the carrier material from the sheet of semi-finished material.

26 Claims, 8 Drawing Sheets

(56) References Cited

U.S. PATENT DOCUMENTS

| | | | |
|---|---|---|---|
| 6,078,165 | A | 6/2000 | Ashtiani et al. |
| 6,144,883 | A | 11/2000 | Kuzma |
| 6,304,787 | B1 | 10/2001 | Kuzma et al. |
| 6,340,879 | B1 | 1/2002 | Blacker |
| 6,421,569 | B1 | 7/2002 | Treaba et al. |
| 6,430,448 | B1 | 8/2002 | Chitre et al. |
| 6,862,805 | B1 | 3/2005 | Kuzma et al. |
| 7,240,416 | B2 * | 7/2007 | Milojevic et al. ............... 29/846 |
| 2002/0137243 | A1 | 9/2002 | Chen et al. |
| 2004/0256146 | A1 | 12/2004 | Frericks et al. |
| 2006/0004432 | A1 | 1/2006 | Parker et al. |
| 2006/0020318 | A1 | 1/2006 | Lenarz et al. |
| 2006/0236532 | A1 | 10/2006 | Schuller |
| 2009/0043358 | A1 | 2/2009 | Dadd et al. |
| 2009/0204177 | A1 | 8/2009 | Parker et al. |
| 2009/0229739 | A1 | 9/2009 | Schuller |
| 2011/0127243 | A1 | 6/2011 | Pufulescu et al. |

FOREIGN PATENT DOCUMENTS

| | | |
|---|---|---|
| WO | WO 00/71063 | 11/2000 |
| WO | 0183855 | 11/2001 |
| WO | 02087685 | 11/2002 |
| WO | 02089907 | 11/2002 |
| WO | WO 2005/004978 | 1/2005 |
| WO | WO 2006/000031 | 1/2006 |
| WO | WO 2009/065127 | 5/2009 |

OTHER PUBLICATIONS

International Preliminary Report on Patentability; International Application No. PCT/AU2004/000920 mailed on Jan. 9, 2006 (5 pages).

Fukami et al., "Ablation of Silicone Rubber Using UV-Nanosecond and IR-Femtosecond Lasers," Japanese Journal of Applied Physics, Published on Jul. 7, 2004, pp. 4240-4241, vol. 43, No. 7A, The Japan Society of Applied Physics (2 pages).

International Search Report. PCT/AU2004/000920. Mailed Nov. 17, 2004.

* cited by examiner

METHOD OF FORMING CONDUCTIVE ELEMENTS

CROSS-REFERENCE TO RELATED APPLICATIONS

The present application is a continuing application of U.S. patent application Ser. No. 10/563,866, filed on Apr. 21, 2006, now abandoned which is a national stage application under 35 USC §371(c) of PCT Application No. PCT/AU2004/000920, entitled "Conductive Elements," filed on Jul. 9, 2004, which claims the priority of Australian Patent No. 2003903532, filed on Jul. 9, 2003. The entire disclosure and contents of the above applications are hereby incorporated by reference herein.

BACKGROUND

1. Field of the Invention

The present invention relates to a method of making conductive elements and in particular, to making patterned conductive elements suitable for use in the manufacture of implantable medical devices.

2. Related Art

Medical devices that are implanted in the body are subject to a large range of design and manufacturing constraints.

Such medical devices need to be as small as possible to ensure they are minimally invasive. The order of size for components can be in the micron scale.

Further, the materials from which the devices are made must be "biocompatible". This means they must have been proven to not to cause any significant adverse reactions in the body as a result of contact with bodily fluids or tissue, such as tissue death, tumor formation, allergic reaction, foreign body reaction (rejection), inflammatory reaction, or blood clotting. Moreover, biocompatibility means the material must not be susceptible to damage from long-term placement in the body.

The material of choice for conductive elements in implantable medical devices is platinum, following extensive trials performed over the years.

Given the above requirements, the manufacturing of wiring and connector components for implantable medical devices has developed into a labor intensive and highly specialized craft.

One particular area where this is evident is in the field of cochlear implants, which have been developed to provide the sensation of hearing to hearing impaired individuals.

A cochlear implant system bypass the hair cells in the cochlea to directly deliver electrical stimulation to the auditory nerve fibers, thereby allowing the brain to perceive a hearing sensation resembling the natural hearing sensation normally delivered to the auditory nerve. U.S. Pat. No. 4,532,930, the contents of which are incorporated herein by reference, describes one type of cochlear implant system.

The intracochlear electrode array has generally been manufactured by positioning a plurality of electrically conductive platinum rings (for example, 22) in a linear array, manually welding electrical conductive wires to each of the electrodes, and then molding a resiliently flexible carrier member about the array. Each of the wires is insulated from one another to minimize unwanted interaction between different electrical components.

In view of the high labor cost and complexity associated with the manufacturing of the conductive elements, a number of manufacturing alternatives have been investigated For example, thin film technology can be used to create electrically conductive features on insulating surfaces on a micron scale. Such techniques include electroforming, vacuum deposition (sputtering, evaporation), and chemical vapor deposition.

However, the metallic films produced by these techniques can feature properties that are different from the corresponding properties of the original, bulk materials used. This results in the materials functioning differently from their intended purpose. Further, the integrity of the biocompatible material must be maintained, by avoiding or reducing any contamination introduced during the manufacturing process.

In the case of platinum, thin film techniques tend to result in cracking and delamination of the platinum. This forms a high impedance path which impairs the functionality of the device.

It is desirable to provide an improved method of manufacturing biocompatible conductive devices in the micron scale.

SUMMARY

According to one aspect of the present invention, a method of forming a patterned conductive element for an implantable medical device, the method comprising:

depositing a supplementary material on a sheet of conductive, parent material to form a sheet of composite material;

applying a carrier material over the supplementary material of the composite sheet to form a sheet of semi-finished material;

removing portions from at least the conductive parent material of the sheet of semi-finished material in accordance with a desired pattern corresponding to a patterned conductive element to be formed; and releasing at least the carrier material from the sheet of semi-finished material.

According to one aspect of the present invention, there is provided a method of forming a patterned conductive element for an implantable medical device, the method comprising the steps of:

depositing a supplementary material on a sheet of conductive, parent material to form a sheet of composite material;

applying a carrier material over the supplementary material of the composite sheet to form a sheet of semi-finished material;

removing portions from at least the conductive parent material of the sheet of semi-finished material in accordance with a desired pattern corresponding to a patterned conductive element to be formed; and releasing at least the carrier material from the sheet of semi-finished material.

According to another aspect of the present invention, there is provided a method of making a sheet of semifinished material, said method comprising the steps of:

depositing a supplementary material on a platinum sheet to form a composite sheet; and applying a carrier material over the supplementary material, to form a sheet of semi-finished material;

wherein the platinum sheet on the semi-finished material has a thickness of not more than approximately 100 µm.

According to another aspect of the present invention, there is provided a method of forming an electrode array for an implantable medical device, said method comprising the steps of:

preparing a semi-finished sheet by depositing a supplementary material on a platinum sheet and then applying a carrier material over the supplementary material;

removing portions from at least the platinum sheet in accordance with a predetermined pattern, the pattern including a linear array of stimulating or recording pads and at least one electrical conduction means extending away from each one of the pads to a location distal from the pad; and releasing the carrier material.

BRIEF DESCRIPTION OF THE DRAWINGS

Various exemplary embodiments of the present disclosure will now be described with reference to the drawings, in which.

DETAILED DESCRIPTION

An example of a process used to make a semi-finished sheet material that can later be used to form an electrode array will now be described with reference to FIG. 1A.

Commencing with Step 11, a sheet of conductive, biocompatible parent material 1 is sourced. This parent material is most usually platinum, although other materials which have been shown to possess the same properties at platinum for the purposes of suitability as a conductive element in an implantable medical device could also be used. Preferably, the platinum sheet is at least 99.95% pure and has a thickness of approximately 20 μm to 40 μm, although other dimensions may be used. In one embodiment, the platinum sheet has a thickness in the range of 10 μm to 200 μm.

Next at Step 12, a supplementary material 2 is deposited on to one side of the platinum sheet 1 to form a new composite sheet 3. In this example, the supplementary material 2 is Titanium Nitride (TiN) and is deposited at a thickness of around 2 μm to 4 μm on the upper surface. Other materials such as Tantalum (Ta), Niobium (Nb), Nickel (Ni), or Iridium (Ir) could also be used.

Preferably, the deposition technique uses the "Magnetron" method, which minimizes high temperatures thought to be a contributing factor to possible contamination.

Alternatively, the deposition technique can be performed using vacuum cathodic arc deposition and more preferably, using a filtered arc deposition system (FADS) that is described for example in U.S. Pat. No. 5,433,836.

FADS uses a macroparticle filter which removes microdroplets of cathode material emitted from the surface of the arcing cathode, which results in a film which is free of microdroplets that are present in films prepared by conventional arc evaporation methods.

Vacuum deposition is the deposition of a film or coating in a vacuum (or low-pressure plasma) environment. Generally, the term is applied to processes that deposit atoms or molecules one at a time, such as in physical vapor deposition (PVD) or low-pressure chemical vapor deposition (LPCVD) processes. It can also be applied to other deposition processes such as low-pressure plasma spraying (LPPS).

After deposition of the supplementary material 2, Step 13 is executed by sourcing and then applying a carrier material to the composite sheet 3, so that the supplementary material 2 is disposed between the parent material 1 and the carrier material 2.

In a first example, the carrier material 2 is a copper sheet and is applied to the composite sheet 3 by co-rolling. This process is known as "roll cladding" and effectively "cold welds" or "crush bonds" the materials together, while reducing the overall thickness of the rolled materials.

Alternatively, the carrier material 4 according to this example can be electroplated to the composite sheet.

Finally, at Step 14, the semi-finished sheet material 5 is produced having the following characteristics:

| | Material | Thickness |
| --- | --- | --- |
| Parent material | Platinum | 20 μm to 40 μm |
| Supplementary material | Titanium Nitride | 0.5 μm to 4 μm |
| Carrier material | Copper | 100 μm |

Figure 1A:
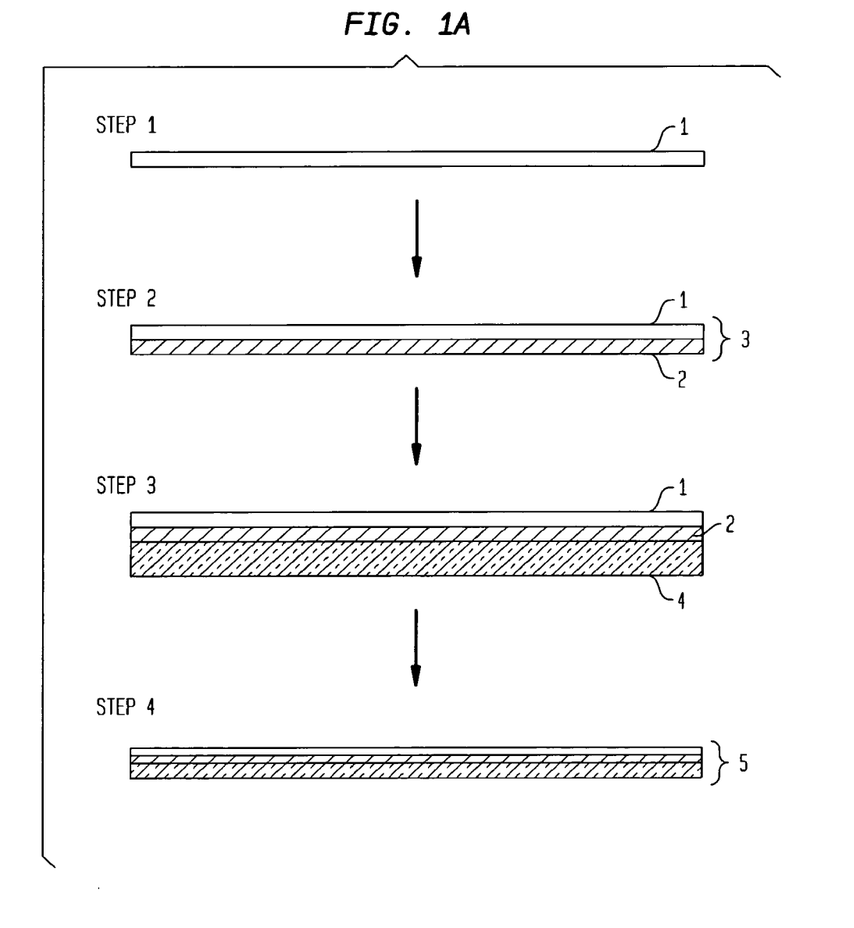
FIG. 1A is a schematic representation of the steps required to manufacture a semi-finished sheet material used to form an electrode array for an implantable medical device in accordance with one embodiment of the present invention.
Figure 1B:
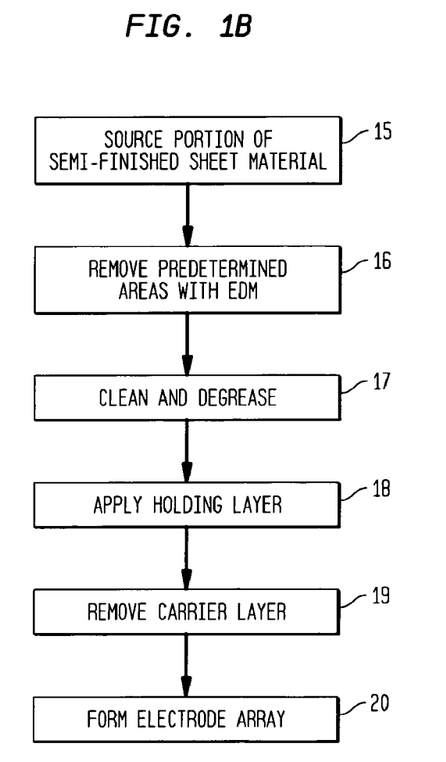
FIG. 1B is a schematic representation of the steps required to manufacture a conductive element for an implantable medical device, starting with the semi-finished sheet material produced by the method of FIG. 1A, in accordance with one embodiment of the present invention.

Referring now to FIG. 1B, an example of a process used to work the sheet of semi-finished material into a patterned conductive element for an implantable medical device will be described. The patterned conductive element has a plurality of conductive paths and in this example, is formed into an electrode array for a cochlear implant. Whilst the example described below uses a micro-machining technique to work the semi-finished material, it is emphasized that the scope of this disclosure includes other methods such as dry etching, where this can be adapted to work for the required micronscale. Similarly, other micro-machining techniques can be used, such as milling or cutting.

Commencing with Step 15, a portion of the sheet of semi-finished material produced by the process of FIG. 1A is cut to a workable size and placed on a work surface of a machine that can perform micromachining, such as electrical discharge machining (EDM). An example of a workable size for the semi-finished material could be approximately 50 mm×250 mm, although this will depend on the actual machine and other routine manufacturing variations.

EDM removes material from an electrically conductive work piece by applying a series of electrical discharges between the electrode and the sheet in a dielectric fluid. The electrode melts and vaporizes the work piece material but never actually touches the work. The size and shape of the tip of the electrode, together with the way in which the electrode is moved around and bought to bear on the surface of the conductive work piece, determines the size and shape of the portions that are to be removed.

At Step 16, the EDM is operated by bringing an electrode tip 21 adjacent the semi-finished sheet material. An example of the configuration of the electrode tip 21 is shown in FIG. 2A.

The EDM process penetrates the platinum parent material, the TiN supplementary material and at least part of the copper carrier material. The copper carrier material is party retained during the EDM process to enable easier, subsequent handling of the fragile platinum material.

Figure 2A:
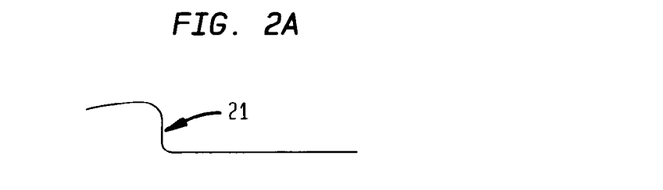
FIG. 2A is a plan view of an electrode tip configuration of an electric discharging machine.
Figure 2B:
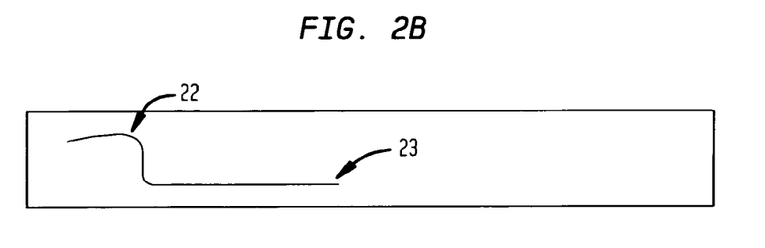
FIG. 2B is a plan view of the semi-finished sheet material showing a line vaporized by use of the tool of FIG. 2A.
Figure 2C:
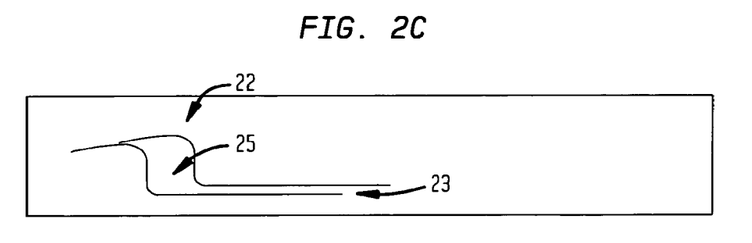
FIG. 2C is a plan view of the semi-finished sheet material of FIG. 2B showing how an electrode and adjoining wire can be formed following a second use of the tool of FIG. 2A.
Figure 2D:
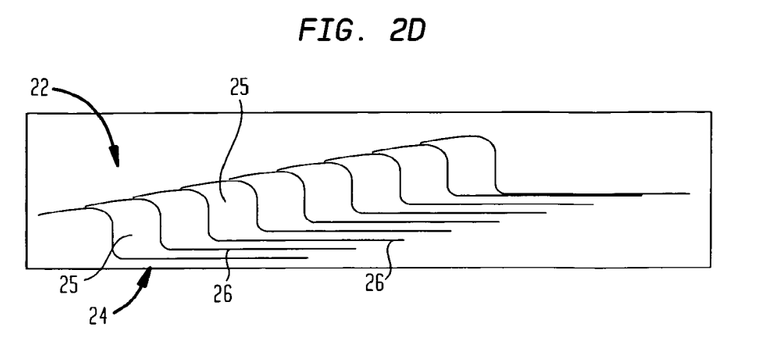
FIG. 2D is a plan view of the semi-finished sheet material of FIG. 2B depicting how an array of electrodes and adjoining wires are formed by a plurality of uses of the tool of FIG. 2A.

In the example of FIG. 2A, the EDM equipment relies on use of a single tip 21 that is brought adjacent the sheet 22 at a number of different locations so as to remove differing portions 23 of the sheet 22. As can be seen in FIG. 2D, multiple use of the single tip electrode 21 at different locations on the sheet 22 gradually leads to the creation of a linear array of discrete, substantially rectangular electrodes 25 or stimulating pads. Each electrode has a conducting portion or wire 24 extending away to a location distal the electrode 25.

Typically, each electrode 25 formed in the sheet 22 has a size of about 0.4 mm$^2$ to 0.5 mm$^2$ and the width of each respective wire is around 100 μm or less, with a similar spacing between neighboring wires.

Figure 4:
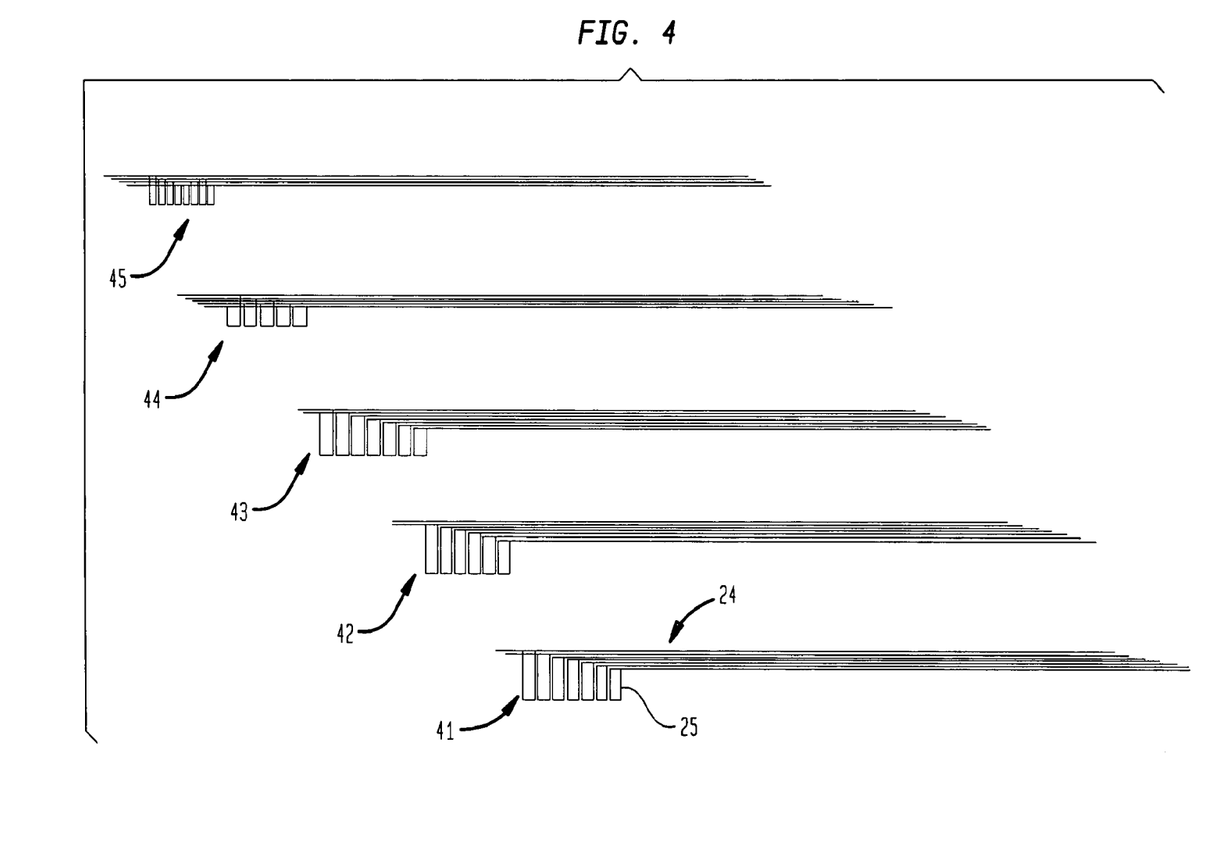
FIG. 4 is a plan view of semi-finished sheet material depicting how different sets of electrodes and adjoining wires can be formed in a platinum sheet through appropriate machining.

As shown in FIG. 4, the linear wires 24 are aligned in a parallel arrangement for at least a portion of their lengths.

Figure 3A:
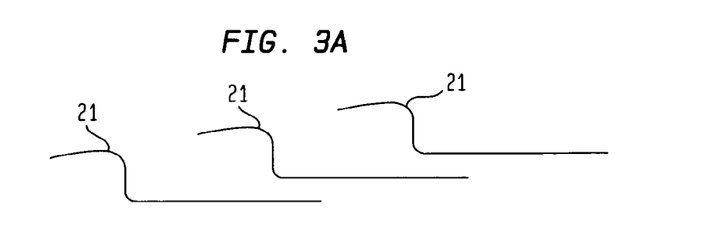
FIG. 3A is a plan view of another electrode tip of an electric discharging machine.
Figure 3B:
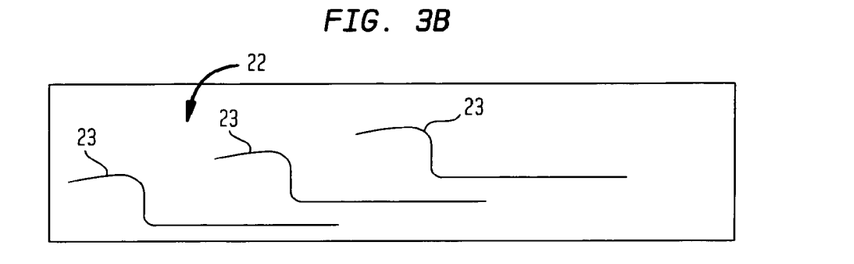
FIG. 3B is a plan view of a semi-finished sheet material showing three lines having been vaporized through use of the tool depicted in FIG. 3A.

FIG. 3A depicts an alternative electrode tip arrangement, in which three separate electrode tips 21 are arranged to simultaneously remove three regions 23 of sheet 22 as depicted, for example in FIG. 3B.

Figure 3C:
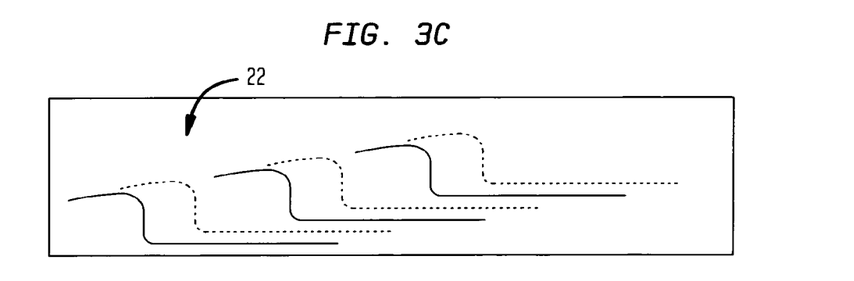
FIG. 3C is a plan view of the semi-finished sheet material of FIG. 3C depicting how three electrodes and adjoining wires can be formed following a second use of the tool of FIG. 3A.
Figure 3D:
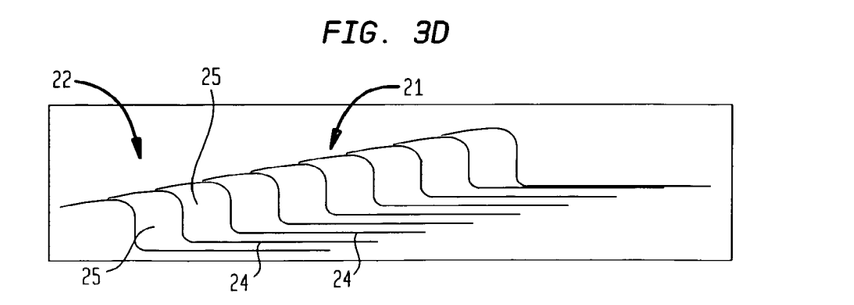
FIG. 3D is a plan view of the semi-finished sheet material of FIG. 3B depicting how an array of electrodes and adjoining wires are formed by a plurality of uses of the tool of FIG. 3A.

As depicted in FIGS. 3C and 3D, through multiple uses of the EDM, an array of electrodes 25 and associated wires 26 are formed in the sheet 22. The advantage of the use of the arrangement depicted in FIG. 3A is that fewer uses of the EDM tip results in the formation of the same array 24.

Having completed the 'working' or micro-machining of the semi-finished material, Step 17, is then performed t. Here, a top side of the worked platinum sheet is cleaned and degreased in preparation for the remaining process steps.

At Step 18, a holding layer is applied to the top side of the worked platinum sheet to increase strength. The holding layer is typically resiliently flexible and also relatively electrically insulating. An example material would be parylene which is typically applied using vapor phase deposition. Alternatively, silicone could be sprayed on to the sheet.

If desired, the electrodes 25 can be masked before the holding layer is applied. Alternatively, the holding layer can be later removed from the electrodes 25, such as by laser ablation, to expose the electrodes.

At Step 19, the layer of copper carrier material is released by way of a chemical etch, for example, by using ammonium persulfate. Where the carrier is copper, this can be achieved by dissolving the copper in a bath. This technique operates on the principle that the copper layer is oxidized and hence dissolved at a potential that is lower than the potential required to oxidize the remaining platinum of the sheet.

Other techniques to remove the carrier material may be utilized in alternative embodiments of the present invention, depending on the material used.

Figure 5:
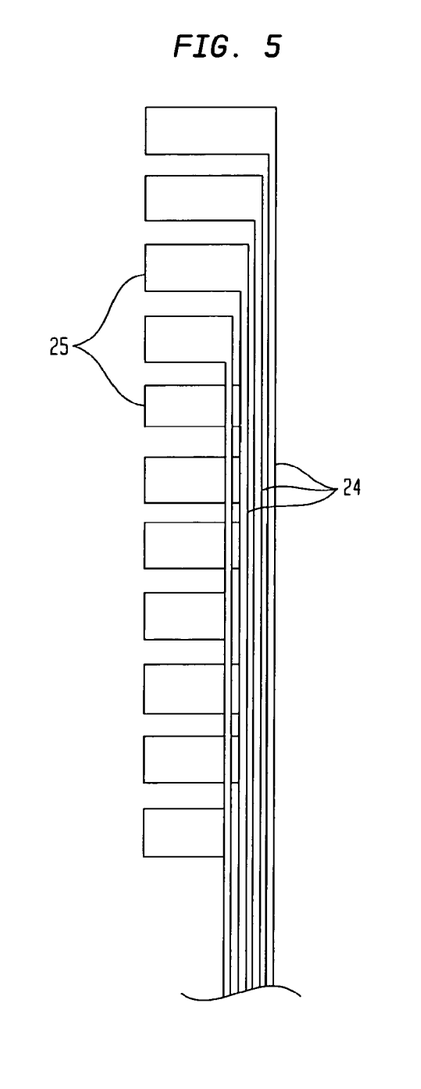
FIG. 5 is a drawing depicting how sets of electrodes formed using an embodiment of the method defined herein can be stacked on top of each other to form an electrode array suitable for use in a cochlear implant system.

Step 20 involves formation of the electrode array, in which the sets of electrodes are stacked one upon the other. The actual position of the electrodes in each set are not necessarily vertically aligned. Rather, the set immediately above its lower set may be laterally offset so as to ensure the electrodes are visible from beneath the stack. An example of a part of a longitudinal array of electrodes 25 is depicted as FIG. 5.

As depicted in FIG. 4, the wires 24 extending from each electrode 25 are of the same length. It can, however, be envisaged that the wires 24 could be formed with different lengths to account for the ultimate offset present when forming the stack.

Once the stack is formed, the electrodes are deformed so as to at least partially extend in a third dimension. Preferably, each of the electrodes are curved out of the plane of the wires 24 for each set of electrodes. The curvature can be substantially semi-circular. A mandrel can be used to form the curvature in the electrodes.

Figure 6:
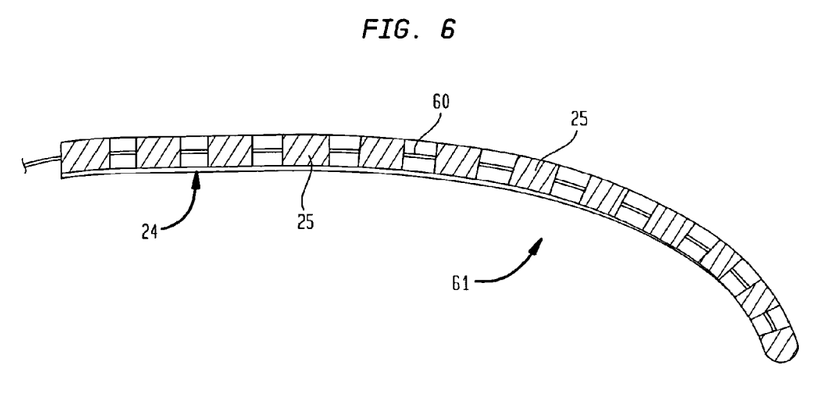
FIG. 6 illustrates a carrier member having an array of curved electrodes with a stylet positioned therein, the carrier being depicted in a configuration ready for insertion into the cochlea of an implantee.

Once the electrodes 25 have been deformed to have a substantially semi-circular curvature, each of the electrodes 25 are further folded about a longitudinal axis of the array 21. This folding of the electrodes 25 serves to bend the electrodes around the wires 24 of the array. The electrodes are folded together and define a lumen that extends through the array 21. An example of the curvature of individual electrodes is depicted in FIG. 6.

Once the electrode array 21 is complete it is encapsulated in a further layer of a biocompatible silicone material to form an electrode carrier member 61. Silastic MDX 4-4210 is an example of one suitable silicone for use in the formation of the carrier member 61. The carrier member can be formed by mounting the array 21 in a mould and filling the mould with silicone and allowing it to cure. In this arrangement, the electrodes are positioned in the mould so as to not be coated with the silicone. In the arrangement depicted in FIGS. 6-8, the carrier member is molded in a spirally-curved configuration and preferentially adopts this configuration unless straightened by the presence of a stylet 60 or other straightening means.

Figure 7:
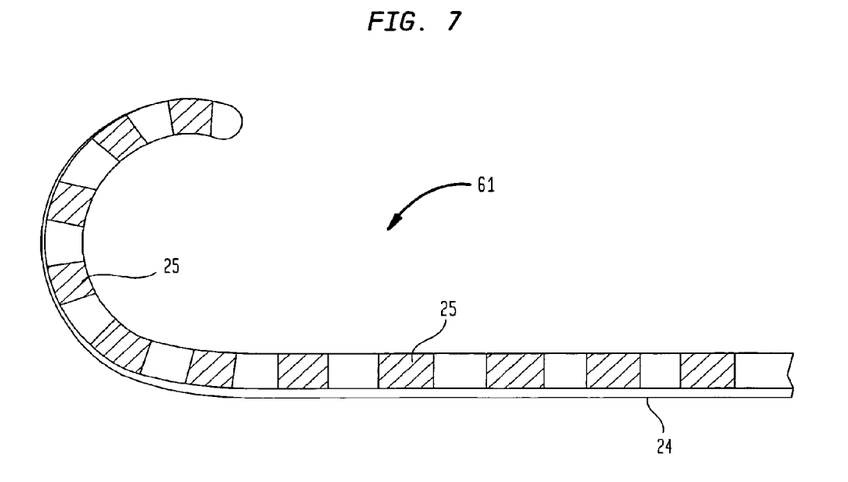
FIG. 7 shows the carrier member of FIG. 6 with the stylet retracted thereby allowing the carrier member to adopt a more pronounced curvature.
Figure 8:
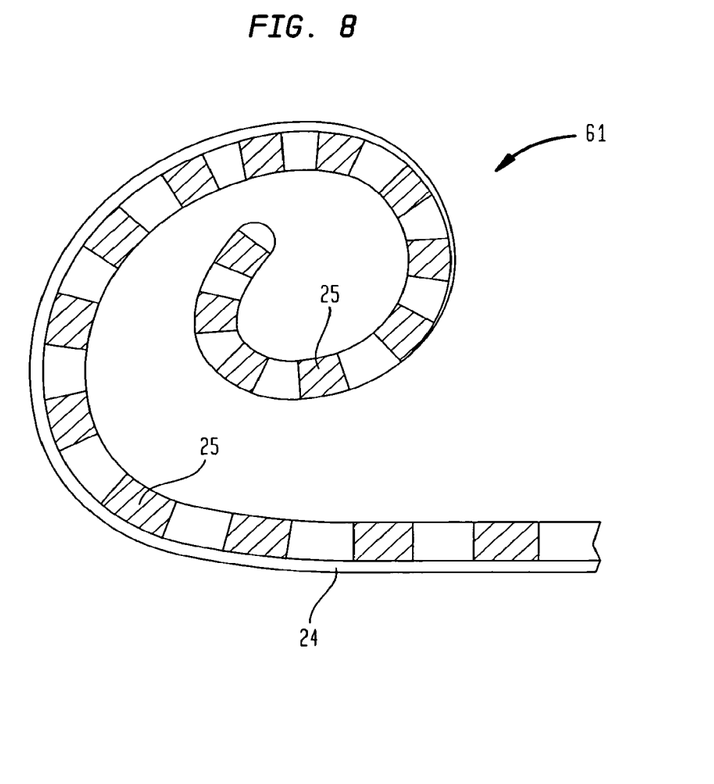
FIG. 8 shows the carrier member of FIG. 6 with the stylet fully retracted thereby allowing the carrier member to adopt its fully curved configuration.

In FIGS. 7 and 8, the degree of curvature of the carrier member is illustrative only. The electrode array and carrier member may be formed and molded, respectively, to adopt a greater or lesser degree of curvature than that depicted when the stylet 60 is fully retracted.

Each of the electrode sets and corresponding wires, are formed in a manner such that their position with respect to each other is predetermined and kept constant throughout the process and in the final product.

While the electrode tip of the EDM equipment is depicted as having a particular arrangement depicted in FIGS. 2A and 3A, it will be appreciated that the electrode tip can have other arrangements. The result of one such other arrangement is depicted in FIG. 4. In this arrangement, use of the EDM tool results in the formation of five different electrodes sets, depicted as 41-45, respectively, on the one platinum sheet.

In FIG. 6, it can be seen that the stylet 60 passes through a lumen in the carrier member 61 formed by the folding of the electrodes 25 as defined above.

The method described herein results in the formation of a carrier member for a cochlear implant system in which there has been no requirement to manually weld a wire to each electrode of the array. This serves to streamline the manufacturing process and allow greater automation thereof, resulting in suitable quality carrier members at a potentially lower cost. Further, the integrity of the platinum is maintained.

It will be appreciated by persons skilled in the art that numerous variations and/or modifications may be made to the invention as shown in the specific embodiments without departing from the spirit or scope of the invention as broadly described. For example, the techniques described could be applied to stimulating devices such as pacemakers, cochlear implants, FES stimulators; recording devices such as neural activity sensors and the like; implantable cables which may be used to connect implantable devices to other implantable devices or stimulating/sensing devices; and diagnostic devices capable of carrying out in-vivo analysis of body parameters.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive

What is claimed is:

1. A method of forming an implantable patterned conductive element for an implantable medical device, the method comprising the steps of:
    depositing a supplementary material on a sheet of conductive, parent material to form a sheet of composite material;
    adhering a carrier material to the supplementary material of the composite sheet to form a second sheet of composite material;
    removing portions from at least the sheet of composite material of the second sheet in accordance with a desired pattern corresponding to a patterned conductive element to be formed; and
    removing at least the carrier material from the patterned second sheet to form the implantable patterned conductive element.

2. The method according to claim 1, wherein the step of adhering the carrier material comprises co-rolling.

3. The method according to claim 2, wherein the conductive parent material is no greater than 2 mm thick before the co-rolling step.

4. The method according to claim 3, wherein the conductive parent material is no greater than 400 μm thick before the co-rolling step.

5. The method according to claim 4, wherein the conductive parent material is no greater than 200 μm thick before the co-rolling step.

6. The method according to claim 5, wherein the conductive parent material is no greater than 150 μm thick after the co-rolling step.

7. The method according to claim 6, wherein the conductive parent material is no greater than 50 μm thick after the co-rolling step.

8. The method according to claim 1, wherein the conductive parent material is biocompatible.

9. The method according to claim 8, wherein the conductive parent material is platinum.

10. The method according to claim 9, wherein the platinum sheet has a thickness being no greater than 100 μm.

11. The method according to claim 10, wherein the patterned conductive element is no greater than 1000 μm thick.

12. The method according to claim 10, wherein the platinum sheet has a thickness no greater than 200 μm.

13. The method according to claim 12, wherein the platinum sheet has a thickness no greater than 40 μm.

14. The method according to claim 8, wherein the conductive parent material is platinum/iridium.

15. The method according to claim 1, wherein the supplementary material is selected from any one of the group consisting of TiN, Ta, Nb, Ni and Ir.

16. The method according to claim 1 wherein the carrier material is conductive.

17. The method according to claim 16, wherein the carrier material is copper or steel.

18. The method according to claim 1, wherein the removing portions from at least the sheet of composite material is performed by micro-machining.

19. The method according to claim 18, wherein the micro-machining includes any one selected from the group consisting of EDM, milling and cutting.

20. The method according to claim 1, further comprising the step of coating the patterned parent material with a layer of resiliently flexible material before the removing at least the carrier material.

21. The method according to claim 1, wherein the removing at least the carrier material is by etching.

22. The method according to claim 1, wherein the parent material remaining after the removing at least the carrier material is at least 99.95% pure.

23. The method according to claim 1, wherein the removing portions from at least the sheet of composite material in accordance with a predetermined pattern, the pattern including a linear array of stimulating or recording pads and at least one electrical conduction means extending away from each one of the pads to a location distal from the pad.

24. The method according to claim 23, wherein the electrical conduction means each has an average width of less than 100 μm.

25. The method according to claim 24, wherein each stimulating or recording pad has an area of less than 0.5 mm$^2$.

26. The method according to claim 25, wherein each electrical conduction means is electrically insulated from its neighbour, the spacing between neighbouring wires being less than 100 μm.

* * * * *